United States Patent [19]

Kinder et al.

[11] Patent Number: 4,963,655
[45] Date of Patent: Oct. 16, 1990

[54] BORON ANALOGS OF AMINO ACID/PEPTIDE PROTEASE INHIBITORS

[75] Inventors: David H. Kinder; Matthew M. Ames, both of Rochester, Minn.

[73] Assignee: Mayo Foundation for Medical Education and Research, Rochester, Minn.

[21] Appl. No.: 199,891

[22] Filed: May 27, 1988

[51] Int. Cl.$^5$ ............................................. C07K 5/08
[52] U.S. Cl. .................................. 530/331; 548/110; 549/213; 560/29; 564/8
[58] Field of Search .......................... 514/64, 18, 19; 530/331; 548/110; 549/213; 560/29; 564/8

[56] References Cited

U.S. PATENT DOCUMENTS 4,499,082  2/1985  Shenvi et al. ........................ 530/331
4,537,773  8/1985  Shenvi ................................ 514/64

OTHER PUBLICATIONS

B. Goz et al., *Biochem. Pharmacol.*, 35, 3587 (1986).
D. H. Kinder et al., *J. Med. Chem.*, 28, 1917 (1985).

*Primary Examiner*—Lester L. Lee
*Attorney, Agent, or Firm*—Merchant, Gould, Smith, Edell, Welter & Schmidt

[57] ABSTRACT

A method of inhibiting protease activity, growth, and colony formation in mammalian tumor cells by boronic acid analogs of amino acids, dipeptides and tripeptides. A method of coupling a boronic acid analog of an amino acid to other N-protected amino acids or N-protected dipeptides and compositions formed from the coupled products.

3 Claims, 6 Drawing Sheets

Cbz-Ala-I-boroValine

Cbz-Ala-I-boroPhenylalanine

Substrate Hydrolysis

Boronic Acid Binding

BORON ANALOGS OF AMINO ACID/PEPTIDE PROTEASE INHIBITORS

BACKGROUND OF THE INVENTION

This invention was made with government support under grant CA 09441 awarded by the National Cancer Institute. The government of the United States has certain rights in this invention.

This invention relates to boron analogs of amino acids and small peptides and the use of the analogs to inhibit growth or colony formation of mammalian cells.

Three major families of antitumor agents are known. Each of the families of agents is associated with a recognized mechanism of action. The families of antitumor agents and associated mechanisms may be defined as follows: First, antitumor agents may be alkylating agents, which generally bind in a covalent manner with DNA to form bifunctional lesions. The bifunctional lesions involve adjacent or nearby bases on the same strand, or alteratively involve bases on opposite strands forming interstrand crosslinks. Second, antitumor agents may be antimetabolites, which generally inhibit enzymes involved in the synthesis or assembly of DNA. Alternatively, an antimetabolite may serve as a fraudulent or analog substrate of DNA processes. Third, antitumor agents may be antibiotics, which work by intercalating into the DNA helix or introducing strand breaks into DNA.

Thousands of potential anticancer agents have been evaluated. Essentially all effective agents (of which very few have been found) appear to work by one of the above-mentioned mechanisms. The subject invention concerns a class of molecules which are not associated with any of the three major families of antitumor agents.

Proteases and protease inhibitors have been reported in association with cancer-related processes. The most common associations involve increased protease enzyme activities or enzyme concentration. Such increased protease activity may be associated with transformation of cells by viruses, chemicals or other agents, as well as with the metastatic potential of cancer cells. Additionally, data have been published which suggest that protease inhibitors may prevent or reduce the incidence of transformation and reduce the metastatic potential of cancer cells. A number of protease inhibitors has been previously evaluated against murine tumor cells in both culture and in whole animals as potential antitumor agents. Most are inert or require very high concentrations to achieve significant tumor cell killing.

The synthesis and protease inhibition properties of Cbz-ala-borovaline and Cbz-ala-borophenylalanine (trivialized names) have been previously reported (Kinder and Katzenellenbogen, *J. Med. Chem.* 28:1917–25, 1985). One of the analogs, Cbz-ala- borophenylalanine, has also been evaluated for cytotoxicity against Lewis lung murine tumor cells in culture (Goz et al., *Biochem. Pharmacol.* VOL/PAGE 1986). The Kinder paper contains no data relating to the potential antitumor activity of these molecules, and the Goz paper found only modest activity against a murine tumor line. Other protease inhibitors have been evaluated in vitro and in vivo as antitumor agents, always with disappointing results.

SUMMARY OF THE INVENTION

The subject invention includes a method of inhibiting protease activity, growth, and colony formation of mammalian cells by boronic acid analogs of amino acids, dipeptides, and tripeptides and the physiologically-acceptable salts thereof. The invention also includes a method of coupling a boronic acid analog of an amino acid to other N-protected amino acids or N-protected dipeptides and compositions including compounds produced by the coupling reactions.

DETAILED DESCRIPTION OF THE PREFERRED EMBODIMENTS

Two of the products of the subject invention have been evaluated as potential anticancer agents. All of the molecules produced by the method of this invention share a basic feature as boronic acid analogs of amino acids. It is believed that the analogs function as protease inhibitors by mimicking the transition state of serine protease-catalyzed peptide hydrolysis.

Both the previously known and the new analogs are inhibitors of the enzymes elastase and chymotrypsin (and quite possibly other proteases). Additionally, the analogs are cytotoxic against human and murine tumor cells in culture. Thus, the analogs are useful as potential anticancer agents.

However, preliminary data on the analogs, most particularly the two named compounds, have been very striking by comparison with other inhibitors. Thus far, growth inhibition and colony formation inhibition of the two named molecules against a human melanoma cell line, a human lung carcinoma cell line, and a murine leukemia cell line (L1210) have been observed. In addition, the analogs demonstrate a lack of inhibition of macromolecular synthesis, specifically DNA and protein synthesis.

Several new Cbz-protected dipeptide and tripeptide analogs have been prepared. In addition, the coumarin analogs of the two named molecules have been prepared by replacing the Cbz protecting group with a fluorescent coumarin derivative to enable imaging and localization of the molecules. The fluorescent analogs are also effective, both as protease inhibitors and as cytotoxic agents, just as are the parent anlogs. Coumarin labeled analogs and tripeptide (as opposed to dipeptide) analogs were prepared from deprotected peptide boroamino esters (by hydrogenolysis) with subsequent coupling of a protected amino acid or coumarin acetic acid to the free amine group using an acyl azide method.

Production of necessary precursors has been explained by Kinder and Katzenellenbogen and similar precursors are described by Shenvi in U.S. Pat. No. 4,537,773 and 4,499,082 which are incorporated herein by reference.

Proteases are ubiquitous enzymes involved in a myriad of cellular activities including digestion, blood coagulation and fibrinolysis, the processing and degradation of proteins, sperm penetration, and have been implicated as important components in regulating cascades. Proteases have also been implicated in transformation, tumor invasion and metastasis. Naturally occurring and synthetic protease inhibitors are believed to interfere with such processes, based upon the effect of the analogs in model systems. Reports exist of modest growth inhibition of cells in culture following exposure to protease inhibitors, such as chloromethyl ketones, soybean trypsin inhibitor, ovomucoid, and aprotinin.

Figure 1:
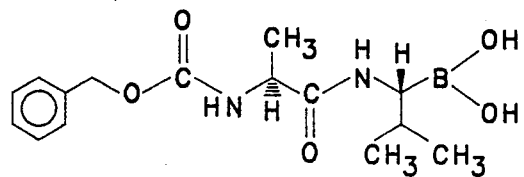
FIG. 1 illustrates the structure of the protease inhibitors Cbz-ala-1-borovaline and Cbz-ala1-borophenylalanine. Synthesis and apparent Ki values are from Kinder and Katzenellenbogen, *J. Med. Chem.* 28:1917, 1985.
Figure 1:
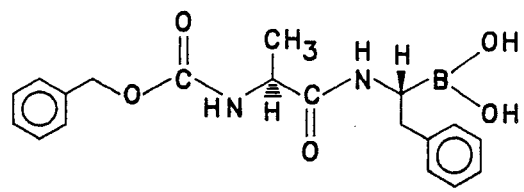
Figure 2:
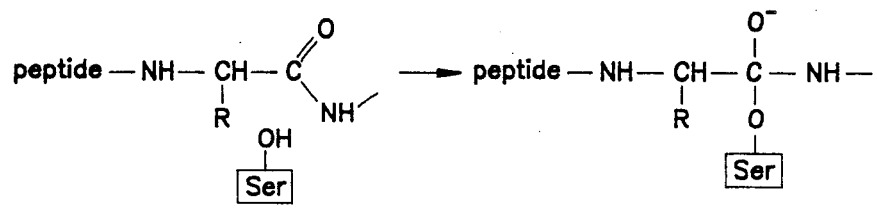
FIG. 2 illustrates serine protease mechanism (upper panel) and inhibitor mechanism (lower panel). See BACKGROUND OF THE INVENTION for explanation.
Figure 2:
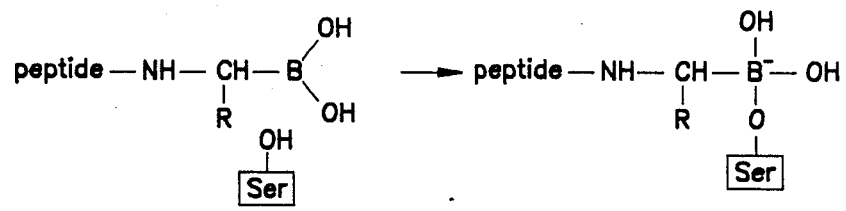

Serine proteases, for example chymotrypsin and elastase, hydrolyse peptide bonds by a nucleophilic attack of the serine-OH in the active site of the enzyme on the carboxyl carbon of the substrate peptide bond. The nucleophilic attack forms a transient $sp^3$ tetrahedral adduct. When boron is substituted for carboxyl carbon at the reactive substrate site (e.g., where hydrolysis occurs), the $sp^3$ intermediate formed following serine-OH attack on the inhibitor is a stable, tight-binding but reversible intermediate (FIG. 1).

Initial growth inibition studies against L1210 murine leukemia cells in culture suggested that the boronic acid analogs of dipeptide compounds were very cytotoxic. Following a 72-hour exposure to 0.03 uM ala-1-borovaline, approximately 50% growth inhibition was observed. The two compounds are also cytotoxic to human tumor cell lines. While not yet fully understood, the mechanism of cytotoxicity is not via macromolecular synthesis inhibition in the human tumor cell lines.

General Methods for Preparation of 1-Acylaminoboronic Acids

Figure 6:
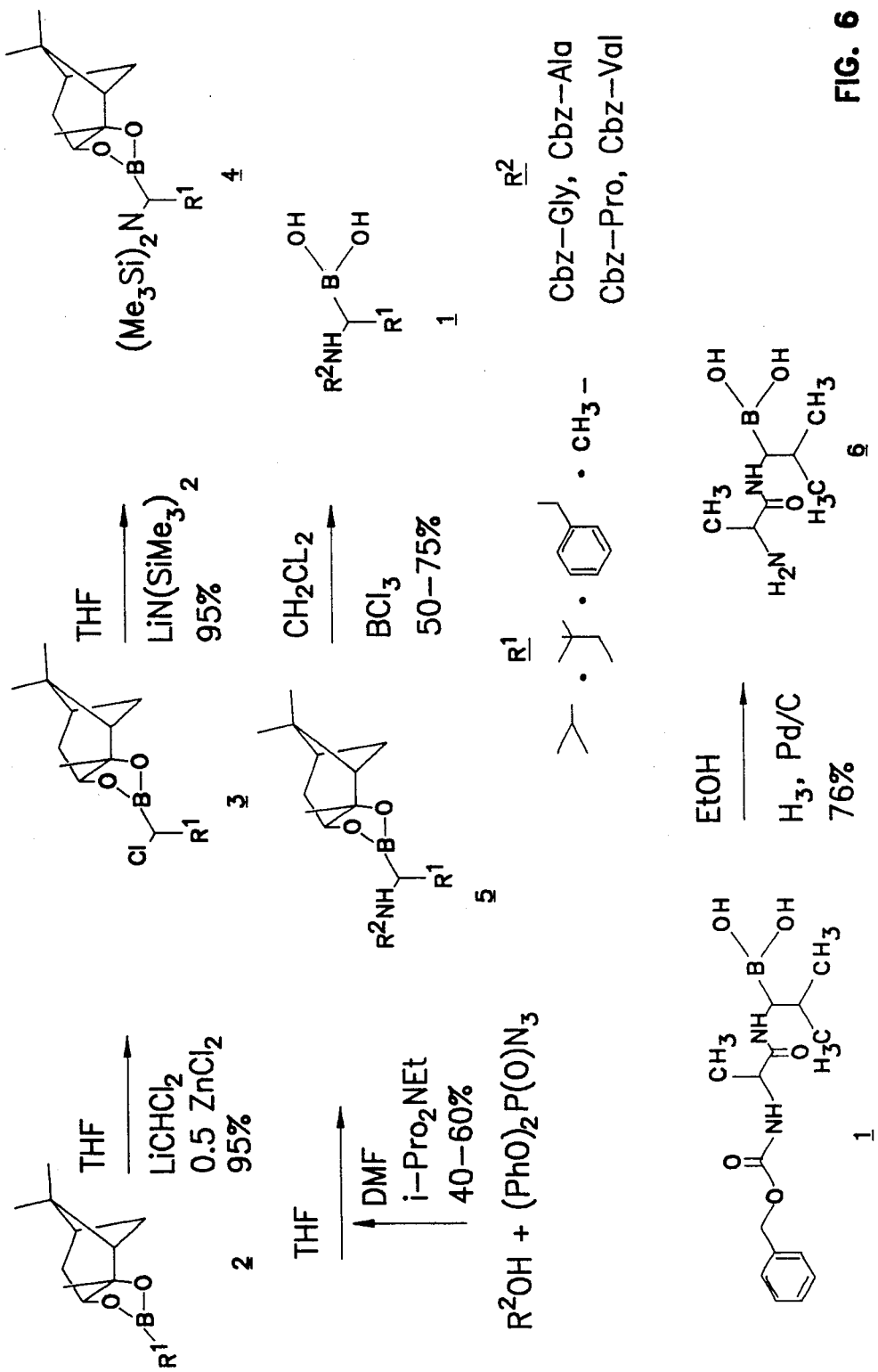
FIG. 6 illustrates the synthetic Scheme I for production of a boron analog I.
Figure 7:
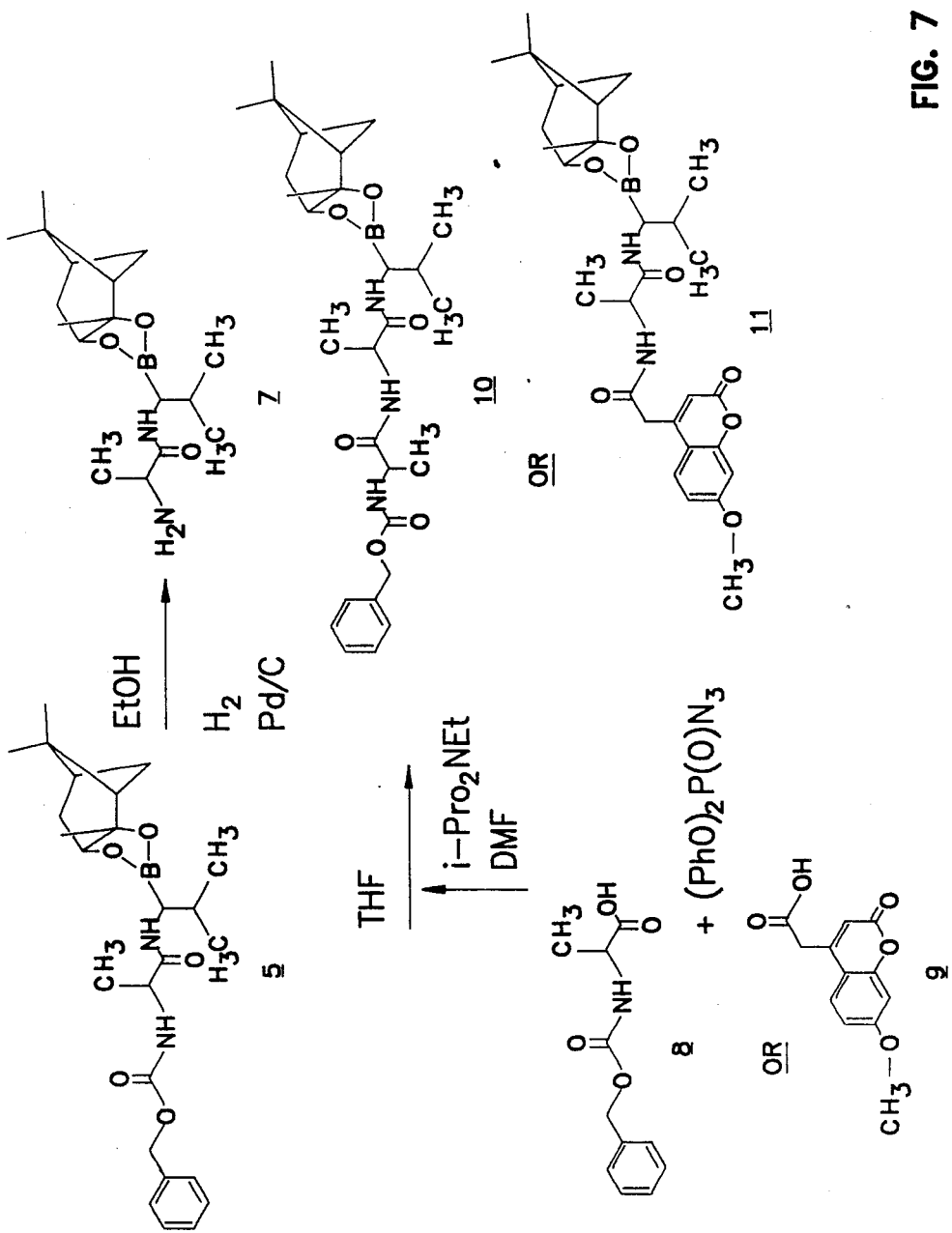
FIG. 7 illustrates the synthetic Scheme II for coupling of additional amino acid residues or other moieties to an N-terminal end of boron analogs.

The general synthetic pathway is outlined in Scheme I as shown in FIG. 6. The boroamino acid analogs 1 are prepared in a stereospecific manner from $(+)-\alpha-$pinanediol boronic esters 2. The stereochemistry of the intermediate chloroboronic esters 3 and 1(bis-trimethylsilyl)aminoboronic esters 4 has been previously disclosed (see Matteson, *J. Am. Chem. Soc.* 103:5241–42, 1981). Coupling of the bis-trimethylsilylaminoboronic esters 4 to various amino acids is hindered by steric interaction of three parts. Specifically, steric bulk in (1) the $R^1$ group, (2) the amino acid to be coupled, and (3) the pinanediol ester moiety, interact to hinder the coupling reaction Additionally, free α-aminoboronic esters are inherently unstable in organic solvents. The instability is generally demonstrated as proteodeboronation.

Utilizing the method of this invention, a wide variety of amino acids can be coupled to pinanediol aminoboronic esters thereby forming compounds of the type 5 in generally modest yields (i.e., from about 40% to about 60%).

Cbz-protected amino acid acyl azides are generated in situ from diphenylphosphoryl azide in the presence of a non-nucleophilic amine, preferably di-isopropyl ethyl amine (i-Pro$_2$NEt) followed by tetrabutyl ammonium fluoride-di-hydrofluoride (n-Bu$_4$NF.2HF). The 1-(bis-trimethylsilyl)amino boronic esters 4 are added to Cbz-protected amino acid acyl azides to remove the trimethylsilyl groups in dimethyl formaldehyde/tetrahydrofuran (DMF/THF) solvent mixtures. Solvent composition is critical to the reaction. In other words, no product is isolated if THF is omitted from the solvent mixture. The non-nucleophilic amine, i-Pro$_2$NEt, is used as base in place of triethane amine (Et$_3$N) (a usual base in peptide coupling reactions) to minimize proteodeboronation faciliated by trimethylammonium salts as observed in previous reactions (see for example: Kinder and Katzenellenbogen, *J. Med. Chem.* 985).

The pinanediol esters are cleaved with 3 mole equivalents of BCl$_3$ in CH$_2$Cl$_2$ at approximately 0° C. to reveal the free boronic acids. The ester cleavage or hydrolysis is in contrast to previously published methods which rely upon destruction of the pinanediol group to liberate the boronic acid (see for example, Kinder and Katzenellenbogen). The hydrolysis reaction of this invention, however, is complete within 5 minutes. The reaction is subsequently quenched by the addition of 1 M NaOH which prevents reformation of the starting pinanediol ester from the liberated pinanediol and aminoboronic acid.

The Cbz-deprotected boro-amino acids can be prepared from 1 by hydrogenolysis in ethanol. The general reaction, illustrated by way of example for the compound ala-borovaline 6, is shown in Scheme I. The analog 6 is produced in 76% yield after recrystallization from minimal volumes of water.

Fluorescent Labeled and Tripeptide Analogs

7-Methoxycoumarin (a fluorescent label analog), and tripeptide analogs are prepared as shown for the borovaline analogs in Scheme II. Following hydrogenolysis of the Cbz group of 5 to 7, a suitably protected amino acid (e.g., alanine [8]) is coupled to the free amino group using the acyl azide method described above to produce 10. Similarly, 7-methoxycoumarin-4-acetic acid (9) can be coupled to 7 to give the fluorescent analog 11.

Removal of the pinanediol ester group is as described above. However, in the particular case of the fluorescent analog 11, care must be taken to minimize destruction of the coumarin moiety by BCl$_3$. Specifically, the 7-methoxycoumarin-4acetate group is converted to 7-methoxy-4-methylcoumarin by BCl$_3$ in excess of the three equivalents needed for pinanediol ester cleavage or upon extended reaction times.

Compounds Which Have Been Prepared

Figure 8:
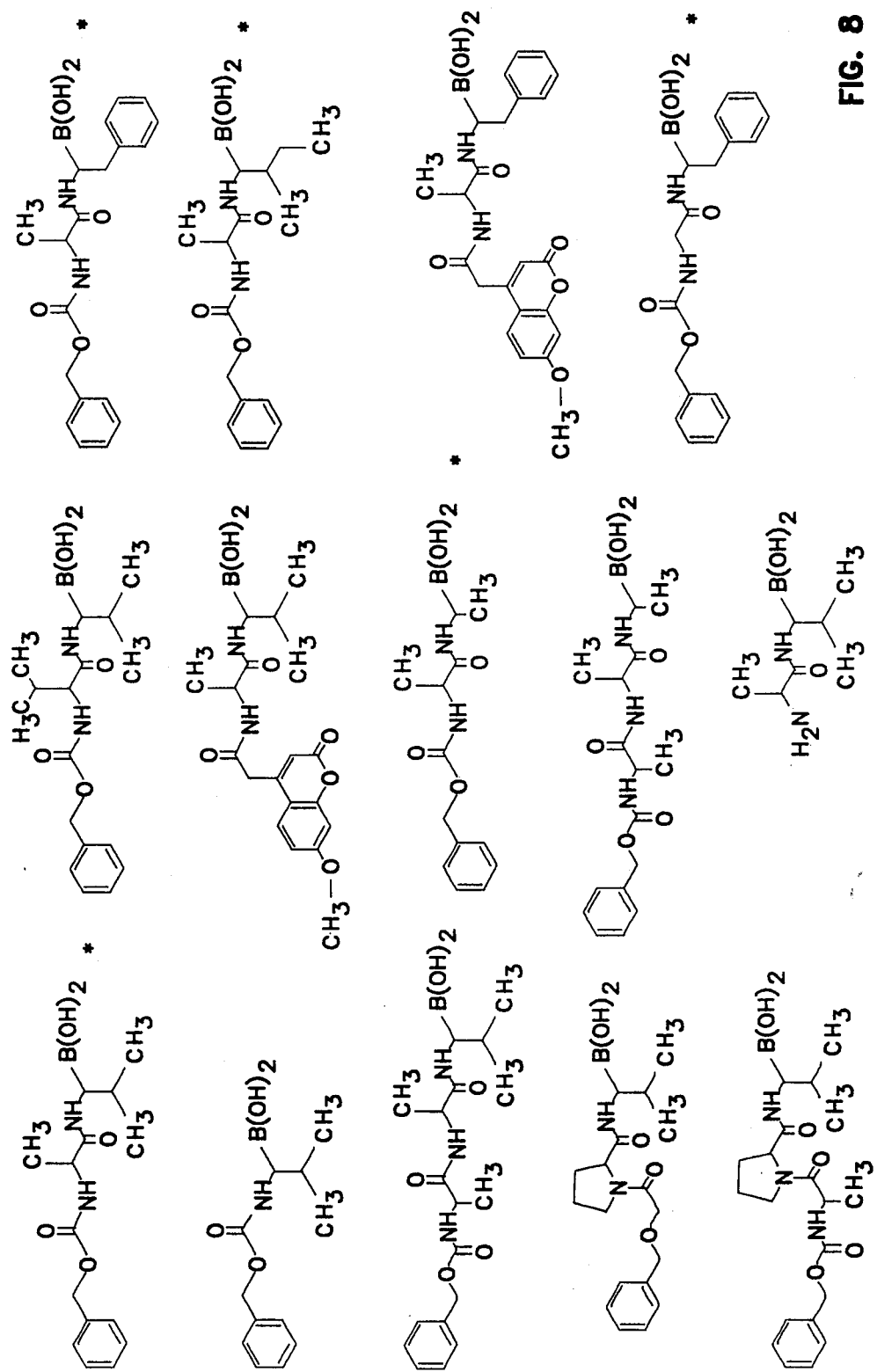
FIG. 8 illustrates boron analogs which have been prepared.

FIG. 8 shows structures of molecules which have been prepared. An asterisk (*) denotes previous production by Kinder and Katzenellenbogen by a different method.

It is believed that the method of the subject invention is also useful in preparing additional compounds of the general type I. Specifically envisioned are compounds modeled on P$_1$ sites of substrates of elastase and chymotrypsin, or other proteases frequently associated with tumor cells. Generally, the compounds are of the type $R_x$-$R_1$ —NH-($P_1$)CHB(OH)$_2$, where $R_x$ is a hydrogen or an amino protective group of fluorescent label, and $R_1$ are amino acids or peptides, independently, in either the (d) or (1) configurations. The choice of $R_1$ is preferably based on known substrate specificity. The boronic amino acid analog is in the (R) configuration which corresponds to the (1) amino acid. The (S) configuration (e.g., (d) amino acid analog) can be established starting from (—)-α-pinanediol boronic esters as described above.

For elastase, preferred $P_1$ side chains are: isopropyl (borovaline), 2-butyl(boro-isoleucine), 2-methylpropyl (boroleucine), methyl (boroalanine).

For α-chymotrypsin, preferred $P_1$ side chains are: benzyl (borophenylalanine), 4-hydroxybenzyl (borotyrosine), 3-CH$_2$-indole (borotyptophan).

For plasmin and plasminogen activator, preferred $P_1$ side chains are: 2-guanidinoethyl (boroarginine), 4-aminopentyl (borolysine). For other proteases $P_1$ side chains include: 2-(methylthio)- ethyl (boromethionine), CH$_2$COX (X = OH, boro- aspartate, X NH$_2$, boroasparagine) CH$_2$CH$_2$COX (X=OH, boroglutamate, X=NH$_2$, boroglutamine).

Growth Inhibition Assay

Human melanoma cells (A375) were seeded at 2 × 10$^4$ cells per tissue culture dish (60×15 mm, Falcon) in Delbecco's Minimal Essential Media (DMEM) containing 10% fetal calf serum and including 1% antibiotics. Cells were allowed to attach for 48 hours prior to exposure to drugs. Cbz-ala-1-borovaline and Cbz-ala-1-borophenylalanine were dissolved in dimethyl sulfoxide (DMSO). The final DMSO concentration in media was 0.5%. Fresh media was exchanged for the media including the drug at appropriate exposure times. Cells were counted after 24, 48 or 96 hours of growth using a Coulter counter. Growth inhibition is expressed as the percent reduction of drug treated cells with respect to untreated control cells.

Colony Formation Assay (CFA)

Human melanoma cells (A375) were seeded at 500 cells per tissue culture dish and allowed to recover for 48 hours. The drug and media mixture was prepared as described above. Following drug exposure, fresh media were substituted for the drug and media mixture. After 7 days, colonies were stained with 0.25% Coomassie Blue and enumerated. Data are expressed as the percent of colonies present in treated plates with respect to control plates (percent survival).

Macromolecular Synthesis Studies

Human melanoma (A375) cells were seeded at 1 × 10$^5$ cells per tissue culture dish 48 hours prior to the addition of the drug (for example, Cbz-ala-1borovaline or Cbz-ala-1-borophenylalanine). The drug and media mixture was prepared as described above. During the last 30 minutes of drug exposure radioactive labeled precursors were added to the media and drug mixture. Specifically, either $^3$H-thymidine (0.2 uCi/ml, to measure DNA synthesis), $^3$H-uridine (0.2 uCi/ml, to measure RNA synthesis, or $^3$H-leucine (1 uCi/ml, to measure protein synthesis) were added. Following 30 minutes at 37° C., the cells were harvested, resuspended in physiological buffered saline (PBS) and the cells counted. An aliquot of the cell suspension was then lysed (10 mM Tris, 1 mM EDTA, 0.1% SDS) and macromolecules were precipitated with ice-cold trichloroacetic acid (TCA) (20%). Following three washes with TCA, radioactivity in the resulting pellet was counted on a Beckman LS2000 Scintillation Counter. Data is expressed as the percentage of counts incorporated into 1×10$^6$ treated cells as compared to 1×10$^6$ untreated cells (percent incorporation).

Figure 4:
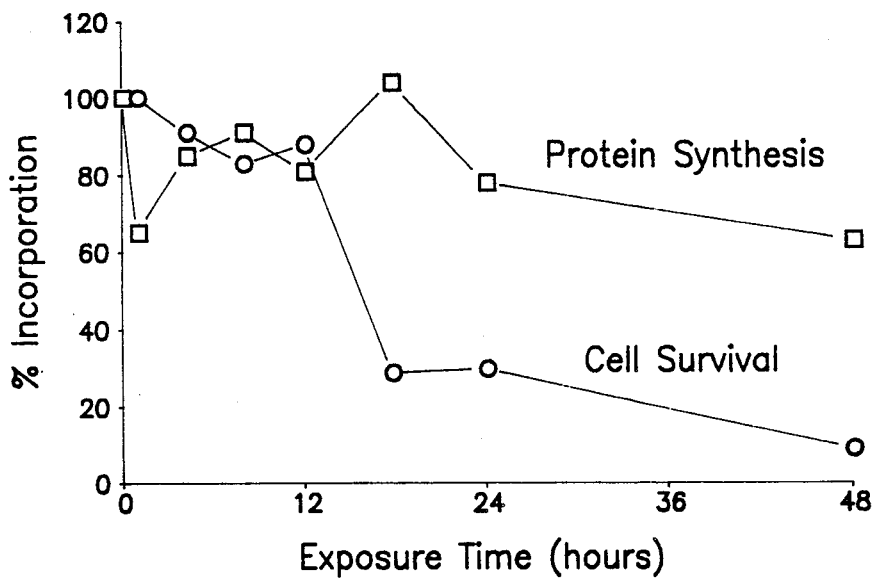
FIG. 4 illustrates inhibition of protein synthesis in A375 cells in culture by Cbz-ala-1borophenylalanine (0.075 ug/ml). Protein synthesis was determined by the incorporation of [$^3$H]-leucine into protein in viable cells.
Figure 5:
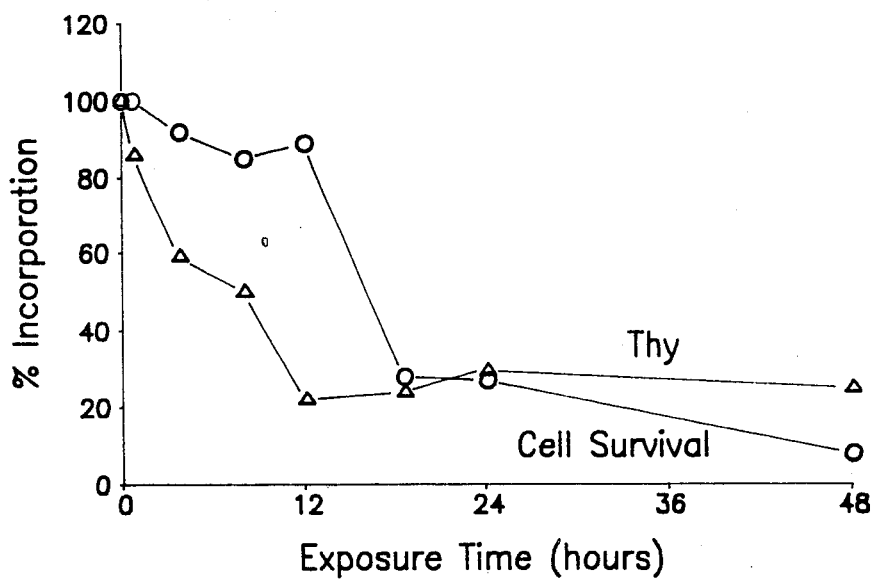
FIG. 5 illustrates inhibition of DNA synthesis in A375 cells in culture by Cbz-ala-1borophenylalanine (0.075 ug/ml). DNA synthesis was determined by the incorporation of [3H]-thymidine into viable cells.

Cbz-ala-1-borophenylalanine did not show an acute inhibition of protein synthesis at a concentration (0.075 ug/ml) which inhibited growth by 70% after 24-hour exposure (FIG. 4). This decrease in protein synthesis follows cell survival and so most likely is a consequence of an injured cell and not a primary mechanism leading to cell death.

Inhibition of Growth/Colony Formation

Figure 3A:
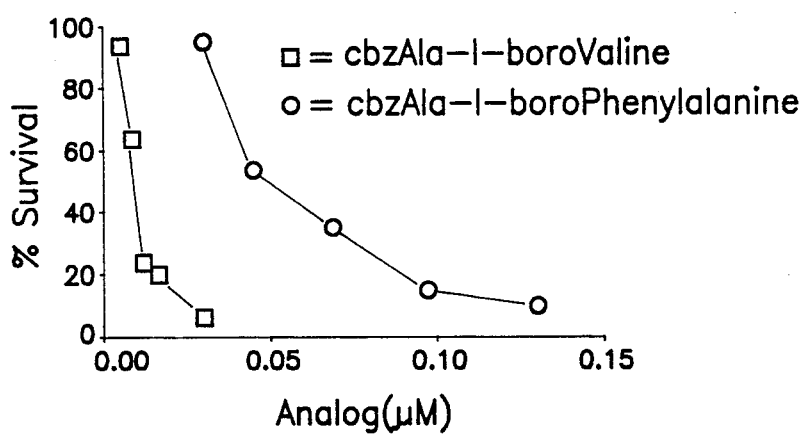
FIG. 3 illustrates colony Formation Assay. Human melanoma cells (A375) were exposed to Cbz-ala-1-borovaline or Gbz-ala-1-borophenylalanine for 1 hour (FIG. 3A), 24 hours (FIG. 3B), or continuously (169 hours) (FIG. 3C). Colonies were enumerated following 7 days of growth each data point represents the average of 5 or more experiments.
Figure 3B:
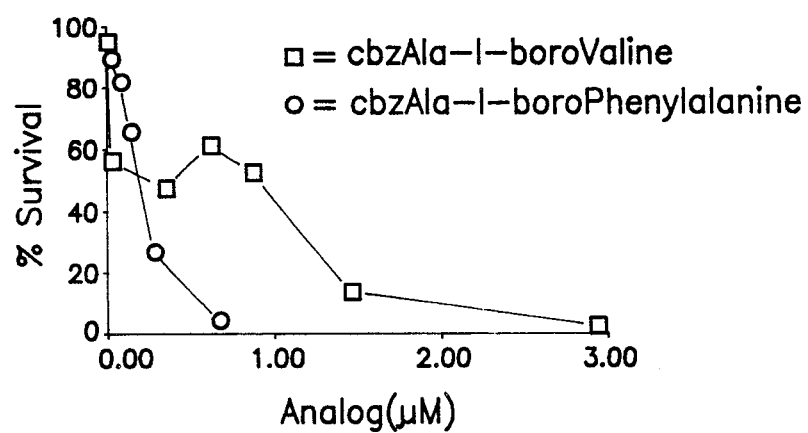
Figure 3C:
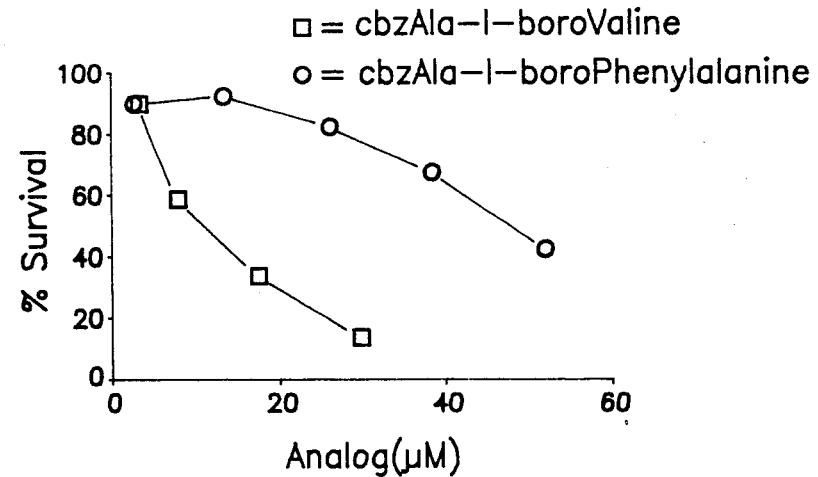

As shown in Table 1, Cbz-ala-1-borovaline and Cbz-ala-1-borophenylalanine were effective inhibitors of the growth and colony formation of human melanoma (A375) and human lung carcinoma (A549) cells in culture. Cbz-ala-1-borovaline was a more potent inhibitor of colony formation than was Cbz-ala-1-borophenylalanine when assayed against human melanoma (A375) cells in culture (FIG. 3). Dose-dependent inhibition of colony formation was observed for both analogs. Qualitatively similar results were obtained against human lung carcinoma (A549) cells in culture (data not shown). A plateau was consistently observed with the 24-hour exposure to ala-1-borovaline between 0.029 uM and 0.833 uM (FIG. 3B). The plateau, however, was not observed in association with the analog after the 1-hour (FIG. 3A) or continuous (FIG. 3C) exposure times. A similar plateau was never observed with Cbz-ala-1-borophenylalanine treatment. A plateau was also seen with A549 cells. A growth inhibition assay (Table 1) yielded qualitatively similar results as the colony formation assay.

Longer exposure times for both analogs led to enhanced inhibition of colony formation for all exposure times (FIG. 3), and enhanced inhibition of growth for the 1-hour versus 24-hour or 96-hour exposure (Table 1). The observed results are consistent with mechanisms involving schedule dependent inhibition. Such mechanisms are possibly explained as a consequence of metabolism or processing of a drug to an active species. However, no difference was observed in the growth inhibition for 24-hour versus 96-hour exposure for either Cbz-ala-1-borovaline or Cbz-ala-1-borophenylalanine (Table 1). The similarity of 24- and 96-hour exposure results on growth inhibition argues against schedule dependent inhibition.

The growth inhibitory activity of other serine protease inhibitors against human melanoma (A375) cells in culture was assessed (Table 2). Negligible growth inhibition was observed following treatment with the inhibitors ovomucoid and aprotinin at concentrations which are very potent for the boron analogs. Another serine protease inhibitor, N-tosylphenylalanine chloromethylketone (TPCK), inhibited growth at very high concentrations. However, at lower inhibition (9% inhibition at 0.284 uM) in the range the boron analogs are very potent (95% inhibition at 0.258 uM ala-1-borophenylalanine).

Preliminary tests of effective boron analogs administered to mice intravenously at doses of approximately 20 mg/kg did not reveal significant toxicity or side effects.

TABLE 1

Growth Inhibition activity of Cbz-ala-1-Borovaline and Cbz-ala-1-Borophenylalanine Human melanoma (A375) cells were exposed to Cbz-ala-1-borovaline or Cbz-ala-1-borophenylalanine for 1, 24 or 96 hours. Cells were counted following 24, 48 or hours of growth. Each data point represents the average of a minimum of 3 experiments. Colony formation data is from FIG. 3C.

| Exposure Time (Hours) | Concentration (uM) | Growth Inhibition (%) 24 hr | 48 hr | 96 hr | Colony Formation Inhibition (%) |
|---|---|---|---|---|---|
| Cbz-ala-1-Borovaline | | | | | |
| 1 | 29.43 | 23 | 48 | 73 | 87 |
| 1 | 7.36 | 14 | 33 | 46 | 41 |
| 24 | 1.47 | 61 | 88 | 93 | 87 |
| 24 | .029 | 17 | 50 | 68 | 43 |
| 24 | .003 | 5 | 5 | 14 | 5 |
| 96 | .736 | 53 | 78 | 89 | — |
| 96 | .029 | 21 | 51 | 68 | — |
| Cbz-ala-1-Borophenylalanine | | | | | |
| 1 | 129 | 42 | .65 | 69 | — |
| 1 | 51.6 | 20 | 41 | 52 | 55 |
| 24 | .645 | 75 | 72 | 98 | 97 |
| 24 | .129 | 41 | 63 | 68 | 35 |
| 24 | .026 | 5 | 3 | 15 | 10 |
| 96 | .258 | 58 | 91 | 95 | — |
| 96 | .1239 | 38 | 68 | 75 | — |

TABLE 2

Growth Inhibition Activity of Selected Protease Inhibitors

Human melanoma (A375) cells were exposed to TPCK (N-tosylphenylalanine chloromethyl ketone), ovomucoid or aprotinin for 96 hours. Fresh inhibitor was added ever 24 hours. Data is from one representative experiment.

| TPCK | | Ovomucoid | | Aprotinin | |
|---|---|---|---|---|---|
| Conc. (uM) | % Inhib | Conc. (uM) | % Inhib | Conc. (uM) | % Inhib |
| 284 | 100 | 89.3 | 5 | 15.4 | 0 |
| 142 | 100 | 17.9 | 0 | 1.54 | 0 |
| 28.4 | 100 | 3.57 | 0 | .154 | 0 |
| 2.84 | 42 | .357 | 1 | .015 | 0 |
| .284 | 9 | .036 | 0 | | |
| | | | | .028 | 5 | .004 | 0 |

TABLE 2-continued

Growth Inhibition Activity of Selected Protease Inhibitors

Human melanoma (A375) cells were exposed to TPCK (N-tosylphenylalanine chloromethyl ketone), ovomucoid or aprotinin for 96 hours. Fresh inhibitor was added ever 24 hours. Data is from one representative experiment.

| TPCK | | Ovomucoid | | Aprotinin | |
|---|---|---|---|---|---|
| Conc. (uM) | % Inhib | Conc. (uM) | % Inhib | Conc. (uM) | % Inhib |
| .028 | 5 | .004 | 0 | | |

These molecules are also useful as antivirol agents, e.g., AIDS virus, Herpes Simplex virus, and antiarthritic agents.

Although the present invention has been described with reference to preferred embodiments, workers skilled in the art will recognize that changes may be made in form and detail without departing from the spirit and scope of the invention.

What is claimed is:

1. A compound of the formula:

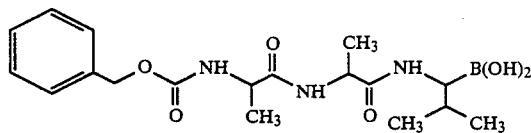

or a physiologically acceptable salt thereof.

2. A compound of the formula:

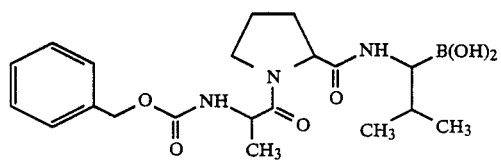

or a physiologically acceptable salt thereof.

3. A compound of the formula:

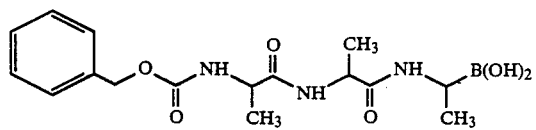

or a physiologically acceptable salt thereof.

* * * * *